United States Patent [19]

Pandey et al.

[11] Patent Number: 4,501,699
[45] Date of Patent: Feb. 26, 1985

[54] MAGGIEMYCIN, ANHYDROMAGGIEMYCIN AND PROCESSES FOR MAKING

[75] Inventors: Ramesh C. Pandey; Margaret W. Toussaint; Jeffrey C. McGuire, all of Frederick; Monica C. Thomas, Columbia, all of Md.

[73] Assignee: Litton Bionetics, Inc., Kensington, Md.

[21] Appl. No.: 438,306

[22] Filed: Nov. 1, 1982

[51] Int. Cl.³ .......................................... C07C 49/798
[52] U.S. Cl. ................................ 260/351.1; 260/376; 260/351.5
[58] Field of Search ............... 260/376, 351.1, 351.5; 435/64, 133, 135, 148, 155, 156, 253, 886

[56] References Cited

PUBLICATIONS

21st Interscience Conference on Antimicrobial Agents and Chemotherapy–Chicago, Ill., (Nov. 1981), Abstract 182.
Maggiemycin and Anhydromaggiemycin: Two Novel Anthracyclinone Antitumor Antibiotics. Isolation, Structures, Partial Synthesis, and Biological Properties", by Ramesh C. Pandey et al.
Arcamone, F.: G. Franceschi, P. Orezzi, G. Cassinell, W. Barbieri & R. Mondelli: Daunomycin I., The Structure of Daunomycinone, J. Amer. Chem. Soc., 86: 5334-5335, 1964.
Arcamone, F.: Daunomycin and Related Antibiotics, In P. G. Sammes (ed.), Topics in Antibiotic Chemistry, vol. 2, pp. 89-239, Halsted Press, New York, 1978.
Arcamone, F., Doxorubicin: Anticancer Antibiotics, Academic Press, New York, p. 195, 1981.
Crooke, S. T.; DuVernay, V. H., Galvar, L. and A. W. Prestakyo; Structure–Activity Relationships of Anthracyclines Relative to Effects on Macromolecular Syntheses, Mol. Pharmacol., 14: 290-298, 1978.
DuVernay, V. H., J. M. Essery, T. W. Boyle, W. T. Bradner and S. T. Crooke, The Antitumor Effects of Anthracyclines, The Importance of the Carbomethoxy Group at Position-10 of Marcellomycin and Rudolfomycin, Mol. Pharmacol., 15: 341-356, 1979.
Hamilton, B.: R. White, J. McGuire, P. Montgomery, R. Stroshane, C. Kalita & R. Pandey: Improvement of the Daunorubicin Fermentation Realized at the 10,000 Liter Fermentor Scale, Advances in Biotechnology, vol. I, 1981, Pergamon Press, New York, pp. 63-68.
Kern, D. L.; R. H. Bunge, J. C. French & H. W. Dion: The Identification of ε-Rhodomycinone and 7-Deoxy-Daunorubicinol Aglycone in Daunorubicin Beers, J. Antibiotics, 30: 432-434, 1977.
McGuire, J. C.: B. K. Hamilton and R. J. White: Approaches to Development of the Daunorubicin Fermentation, Process. Biochem., 14: 2-5, 1979.
McGuire, J.; M. Thomas, R. Pandey, M. Toussaint & R. White: Biosynthesis of Daunorubicin Glycosides: Analysis with Blocked Mutants, Advances in Biotechnology, vol. III, 1981, pp. 117-122, Pergamon Press, New York.
Oki, T.: New Anthracycline Antibiotics, Jap. J. Antibiotics 30, (Suppl.) 570-584, 1977.
Pandey, R. C.; C. C. Kalita, R. J. White & M. W. Toussaint: Process Development in the Purification of Daunorubicin from Fermentation Broth, Process. Biochem., 14: pp. 6-13, 1979.
Pandey, R. C. & M. W. Toussaint: High-Performance Liquid Chromatography and Thin-Layer Chromatography of Anthracycline Antibiotics, Separation and Identification of Components of the Daunorubicin Complex from Fermentation Broth, J. Chromatogr., 198: 407-420, 1980.
Strauss, D. G.: Anthracyclines–Modern Tumor–Inhibiting Agents, Folia Microbiol., 23: 152-161, 1978.
Vanek, Z.; J. Tax, I. Komersova, P. Sedmera & J. Vokoun: Anthracyclines, Folia Microbiol., 22: 139-159, 1977.

Primary Examiner—Glennon H. Hollrah
Assistant Examiner—Raymond Covington
Attorney, Agent, or Firm—Spencer & Frank

[57] ABSTRACT

New anthracyclinones, including maggiemycin, anhydromaggiemycin and 7-oxidodaunorubicinone, have been prepared. Maggiemycin, anhydromaggiemycin, and 7-oxidodaunorubicinone all exhibit biological activity; they are toxic to cell lines KB, L1210 and P388.

4 Claims, 10 Drawing Figures

| | —CH₃ | —CH₂— | ⟩CH— | =CH— |
|---|---|---|---|---|
| ε-Rhodomycinone, C₂₂H₂₀O₉ | 1.23 t (J=7 Hz) <br> 3.81 s | 1.76 m (J=7 Hz) <br> 2.36 d (J=4 Hz) | 4.36 s <br> 5.44 t (J=4 Hz) | 7.37 dd (J=8, 2 Hz) <br> 7.76 t (J=8 Hz) <br> 7.83 dd (J=8, 2 Hz) |
| Maggiemycin, C₂₂H₁₈O₉ | 1.15 t (J=7 Hz) <br> 3.80 s | 1.75 m <br> 2.80 dd (1H, J=17, 2 Hz) <br> 3.20 d (1H, J=17 Hz) | 4.57 d (J=2 Hz) | 7.38 dd (J=8, 2 Hz) <br> 7.72 t (J=8 Hz) <br> 7.90 dd (J=8, 2 Hz) |
| Anhydromaggiemycin, C₂₂H₁₆O₈ | 1.3 t (J=7 Hz) <br> 4.03 s | 2.72 q (J=7 Hz) | | 7.22 s <br> 7.28 dd (J=8, 2 Hz) <br> 7.73 t (J=8 Hz) <br> 8.06 dd (J=8, 2 Hz) |

All spectra were run on XL-100 in CDCl₃.

ANTHRACYCLINONES

| | ED$_{50}$ (µg/ml) | | |
|---|---|---|---|
| | KB | L1210 | P388 |
| MAGGIEMYCIN | 2.70 | 5.20 | 4.40 |
| ANHYDROMAGGIEMYCIN | 0.51 | 0.26 | 0.62 |
| ε-RHODOMYCINONE | | 30.0 | 26.0 |

ANTHRACYCLINONES

| | ED$_{50}$ (µg/ml) | | |
|---|---|---|---|
| | KB | L1210 | P388 |
| 7-OXIDODAUNORUBICINONE | 5.6 | 1.9 | 3.4 |
| ANHYDRO-7-OXIDODAUNORUBICINONE | | 16.0 | 47.0 |
| DAUNORUBICINONE | >100 | 8.9 | 21.6 |

MAGGIEMYCIN, ANHYDROMAGGIEMYCIN AND PROCESSES FOR MAKING

The invention described herein was made during the course of work performed under National Cancer Institute, Department of Health and Human Services, Contract No. NO-1-CO-75830.

FIELD OF THE INVENTION

The invention relates to new anthracyclinones, including maggiemycin, anhydromaggiemycin, and 7-oxidodaunorubicinone.

BACKGROUND OF THE INVENTION

Anthracyclinone antibiotics have provoked considerable interest in recent years because of their impact on cancer chemotherapy. In particular, daunorubicin has been described by Z. Vanek, et al.: "Anthracyclines" in *Folia Microbiol.*, Vol. 22, pages 139 to 159 (1977). *Adriamycin* has been described by T. Oki: "New Anthracycline Antibiotics" in *Jap. J. Antibiotics*, Vol. 30 (Suppl.), pages 570 to 584 (1977); and carminomycin has been described by D. G. Strauss: "Anthracyclines-Modern Tumor-Inhibiting Agents" in *Folia Microbiol.*, Vol. 23, pages 152 to 161 (1978). Most of the biologically active anthracyclines are glycosides with one or more sugar residues attached to the aglycone part. It has been shown by various workers that the whole molecule is necessary for biological activity. No biological activity has been reported for any anthracyline aglycone. F. Arcamone has stated in his recent book: ". . . . In the anthracycline antibiotics, the presence of the amino sugar residue is an important structural requirement for bioactivity, as a biological action due to the isolated aglycone moiety has never been recorded . . . ".

SUMMARY OF THE INVENTION

The present invention provides for the fermentation, isolation, structures, synthesis and biological properties of novel anthracyclines which do not have any sugar residue, and which have been found active in vitro against KB, P388 and L1210 murine tumor cell lines. Structures of these novel anthracyclines are proposed based on their ultraviolet-visible, infra-red, proton nuclear magnetic resonance, and carbon-13 nuclear magnetic resonance spectra, electron impact and high resolution electron impact mass spectra, and confirmed by partial synthesis and a direct correlation with $\epsilon$-rhodomycinone.

DETAILED DESCRIPTION OF THE INVENTION

Figure 8:
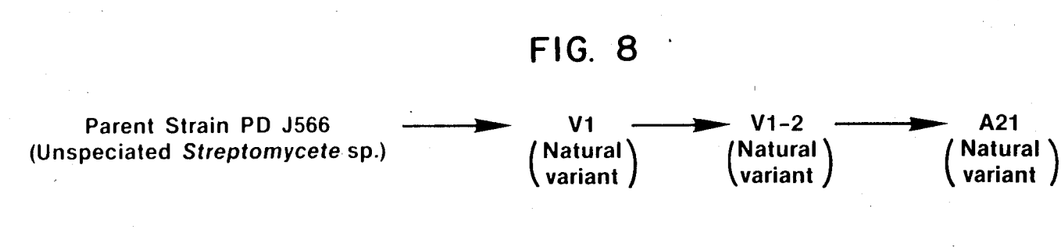
FIG. 8 is a flow scheme illustrating the origin of natural variant strain PD J566-A21 from the parent strain PD J566, an unspeciated Streptomyces sp.
Figure 9:
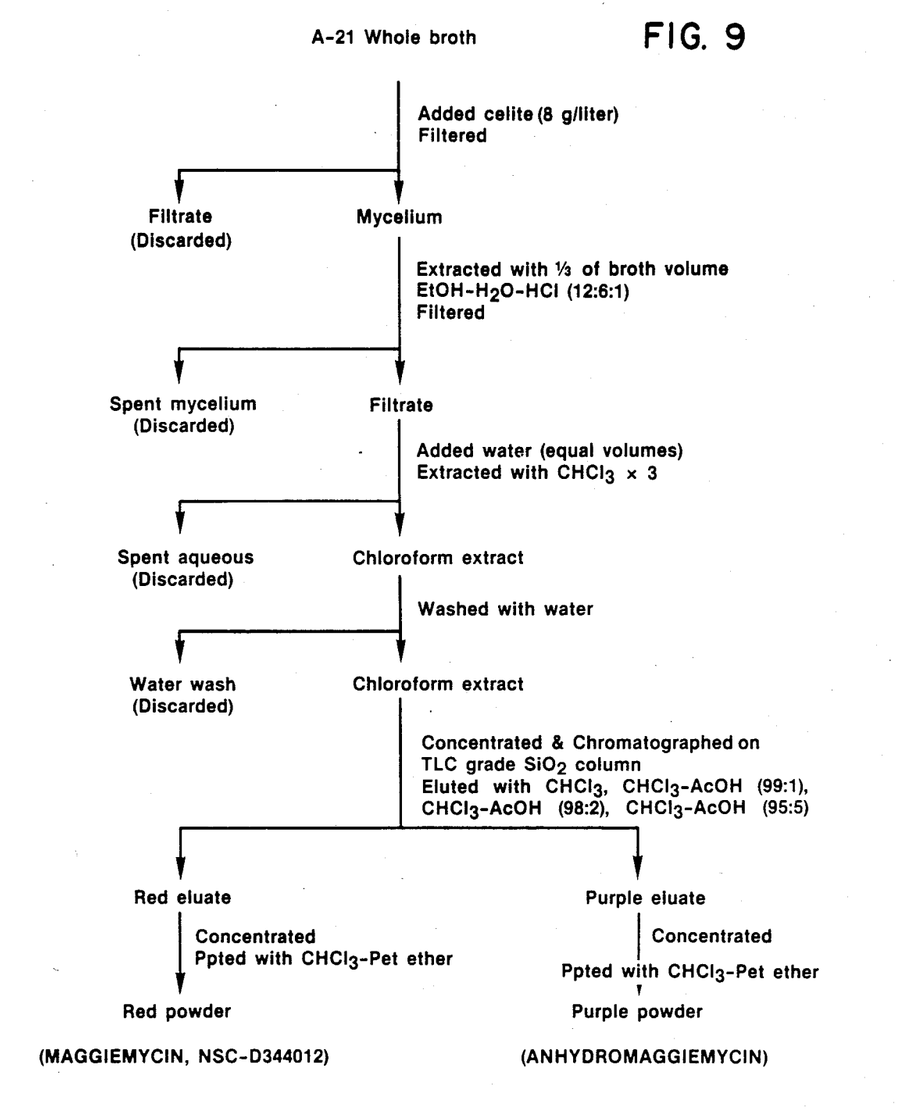
FIG. 9 is a flow scheme for the isolation and purification of maggiemycin (NSC-D344012) and anhydromaggiemycin from A21 whole broth.

FIG. 8 is a flow diagram showing the derivation of the mutant which produces two of the compounds of the invention. It was found that a natural variant strain PD J566-A21, recognized by its formation of blue colonies on nutrient agar and obtained through natural variants V-1 and V1-2 from parent strain PD J566, produced fast-moving antimicrobial and antitumor antibiotics when cultured in a suitable medium. The bioautography of this fermentation extract repeatedly showed biological activity in the region where there was no activity in earlier daunorubicin fermentations. It was of interest, therefore, to isolate these fast-moving biologically active components and determine their structures and biological activity. The isolation of these components from the whole broth is shown in FIG. 9.

The A-21 whole broth was filtered, after addition of about 8 g/liter of celite. The mycelium containing the biologically active material was then extracted with an acidic polar solvent such as about ⅓ volume of a mixture of ethanol-water-hydrochloric acid (12:6:1) and filtered. About an equal volume of water was added to the filtrate and was extracted three times with a polar solvent such as chloroform. The combined chloroform extract was washed with water and concentrated under vacuum to afford the crude compound.

A suitable solvent system was developed for the isolation of pure compounds of the invention by using the following systems in TLC. (A) chloroform (100%), (B) chloroform-ethyl acetate (80:20), (C) chloroform-acetone (80:20), (D) chloroform-methanol (80:20), (E) chloroform-acetic acid (95:5), (F) chloroform-acetone-acetic acid (90:8:2), (G) chloroform-hexane-acetic acid (50:50:5), (H) ether-petroleum ether (1:1), (I) chloroform-benzene methanol (6:3:1), (J) chloroform-benzene-methanol (7:3:2), (K) benzene-ethylacetate-methanol-formic acid-water (5:5:1.5:1:0.3), (L) chloroform-hexane-methanol (5:5:1) and (M) chloroform-heptane-methanol-acetic acid (40:40:18:2). In some of the solvents the order of elution changed. It was found that when the TLC plate was developed first in chloroform and then chloroform-acetic acid (95:5), the purple spot moved far ahead of the red spot. The crude compound was therefore chromatographed on a TLC grade silica gel column eluting with chloroform (100%), chlorform-acetic acid (99:1), chloroform-acetic acid (98:2), and chloroform-acetic acid (95:5). Based on the TLC, various fractions were combined to produce a red and purple eluate. These were separately concentrated and precipitated with chloroform-petroleum ether to yield red and purple powder. The red powder has been designated as maggiemycin (NSC-D344012) and the purple powder as anhydromaggiemycin. Both these compounds were active against *Bacillus subtilis* and *Straphylococcus aureus*. The in vitro antitumor activity of maggiemycin and anhydromaggiemycin against KB, P388 and L1210 murine cell lines is shown in Table 1. From the table it is clear that both the antibiotics are active against these cell lines, although anhydromaggiemycin is more active than maggiemycin.

TABLE 1

In vitro Cytotoxicity of Maggiemycin and Anhydromaggiemycin

| | $ED_{50}$ ($\mu g/ml$)* | | |
|---|---|---|---|
| | KB | L1210 | P388 |
| Maggiemycin | 2.70 | 5.20 | 4.40 |
| Anhydromaggiemycin | 0.51 | 0.26 | 0.62 |

*The dose levels of pure compounds at which 50% inhibition of growth in vitro is noted vs. untreated controls.

The physicochemical properties of maggiemycin and anhydromaggiemycin are summarized in Table 2. Maggiemycin, a red powder, has a melting point of 190°–195° C., $[\alpha]_D^{21} +4.6°$ (c 0.1, Dioxane) and was analyzed for $C_{22}H_{18}O_9$ by high resolution electron impact mass spectrum (HREIMS), m/z 426.0947 (M+).

Anhydromaggiemycin, a purple powder, has mp 252°–256° C. and no optical rotation. It was analyzed for $C_{22}H_{16}O_8$ by HREIMS (m/z 408.0840, M+).

TABLE 2

Properties of Maggiemycin and Anhydromaggiemycin

| | Maggiemycin (NSC-D344012) | Anhydromaggiemycin |
|---|---|---|
| Producing Organism | streptomycete sp., PD J566-A21 | streptomycete sp., PD J566-A21 |
| Appearance | Red powder | Purple powder |
| M.P.(°C.) | 190–195 | 252–256 |
| $[\alpha]_D^{21}$ | +4.6° (Dioxane) | |
| $UV_{\lambda max}^{MeOH}$ nm($\epsilon$) | 240 (36,435) | 262 (31,515) |
| | 285 (10,364) | 325sh (5,372) |
| | 502 (14,023) | 515sh (10,922) |
| | | 550 (16,832) |
| | | 590 (16,921) |
| Mole. Wt. | 426.0947 ($\Delta m = 0.3$ mmu) | 408.0840 ($\Delta M = 0.5$ mmu) |
| Mole. formula | $C_{22}H_{18}O_9$ | $C_{22}H_{16}O_8$ |
| $R_f$* S1 | 0.69 | 0.62 |
| S2 | 0.57 | 0.31 |
| S3 | 0.82 | 0.29 |

*Using analytical TLC silica gel plates. Solv. Syst. S1: Chloroform-benzene-methanol (6:3:1); S2: Chloroform-hexane-methanol (5:5:1); S3: Chloroform:acetone (80:20).

Structures of Maggiemycin and Anhydromaggiemycin

Figure 1:
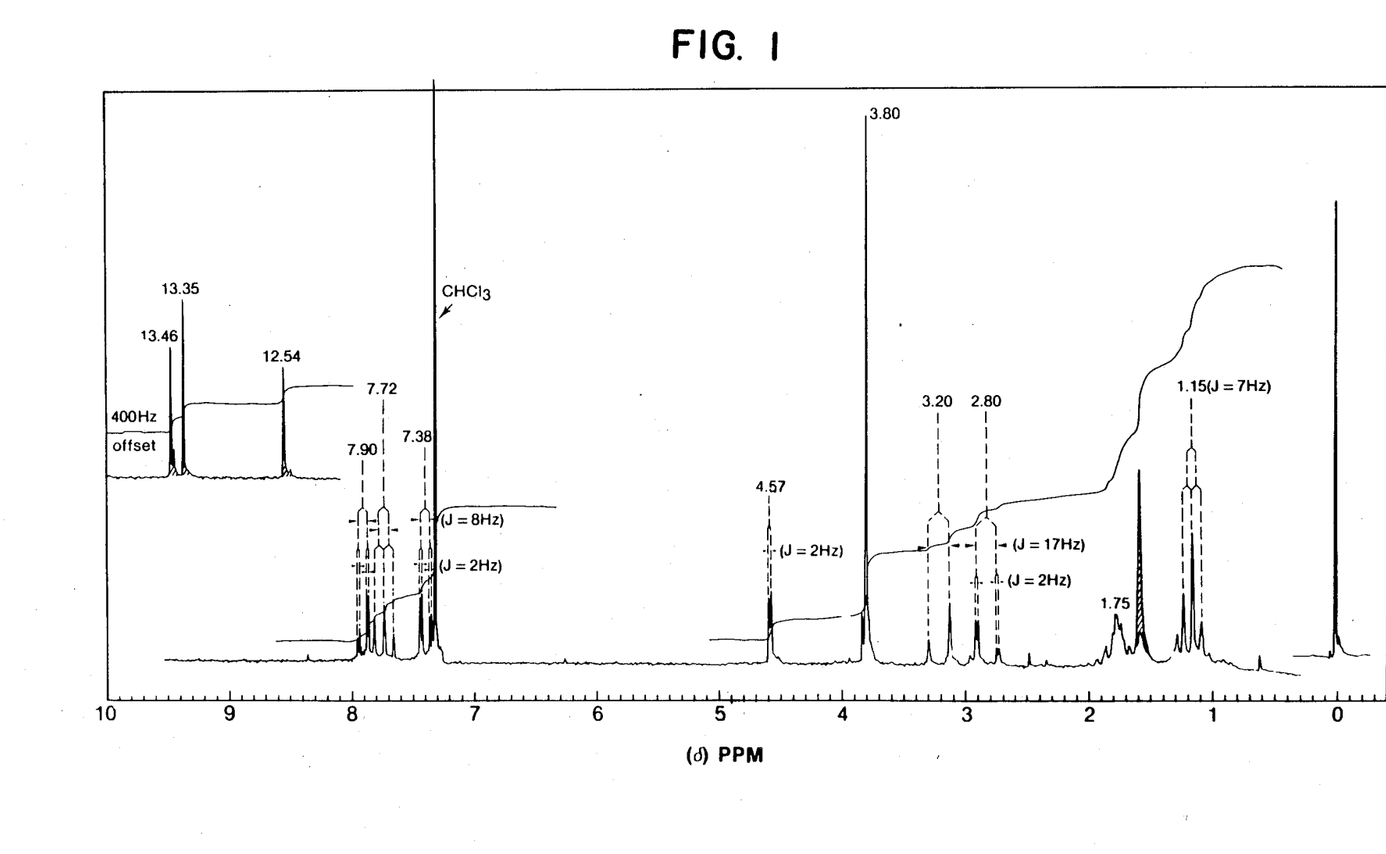
FIG. 1 illustrates the proton nuclear magnetic resonance ($^1$H NMR) spectrum (100 MHz) of maggiemycin in CDCl$_3$. The shaded peaks disappear on D$_2$O shaking.

From the Rf, UV, molecular weights, elemental composition (Table 2) and biogenetic consideration of maggiemycin and anhydromaggiemycin, it is clear that these two new compounds fall into the anthracycline group of antibiotics and are probably anthracyclinones of the $\epsilon$-rhodomycinone or daunorubicinone type. The $^1$H NMR spectrum of maggiemycin (FIG. 1) was reminiscent of the $\epsilon$-rhodomycinone group of antibiotics (methyl triplet centered at 1.15 (J=7 Hz) and methoxy singlet at 3.80 ppm), suggesting that it did not belong to the daunorubicinone type.

Figure 2:
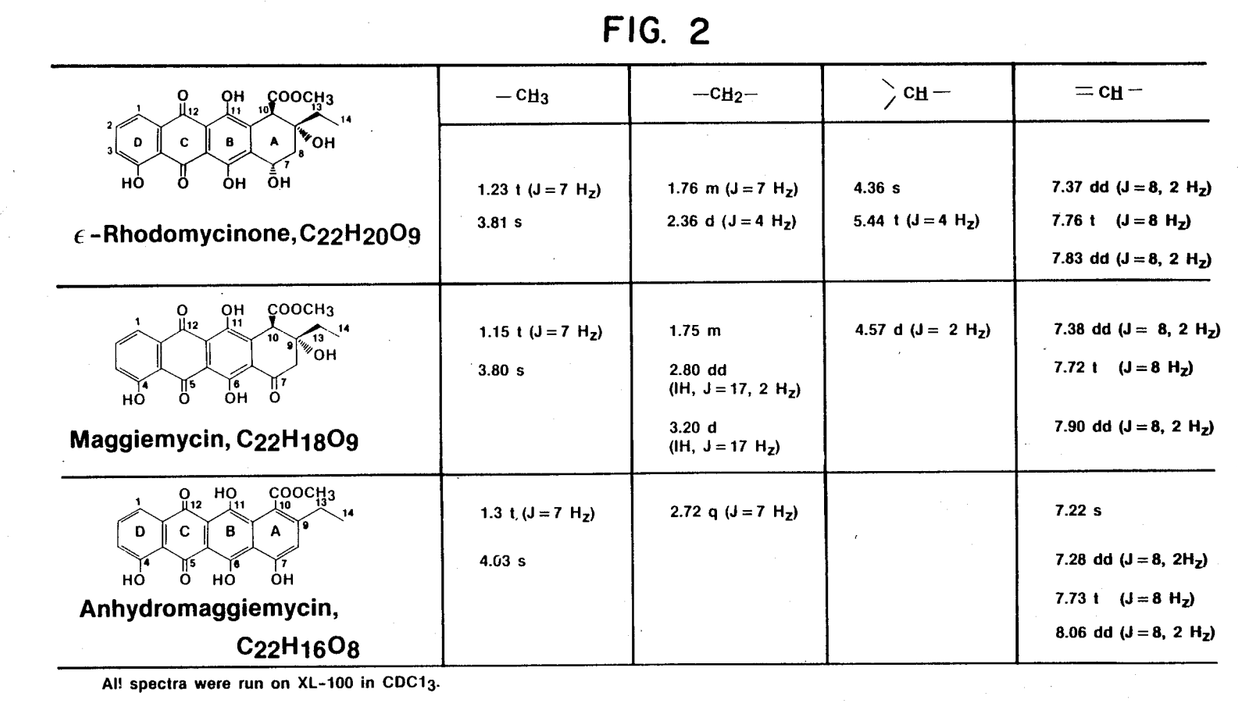
FIG. 2 is a comparison of $^1$H NMR chemical shifts of $\epsilon$-rhodomycinone, maggiemycin and anhydromaggiemycin.

A comparison of the $^1$H NMR spectra of $\epsilon$-rhodomycinone with maggiemycin and anhydromaggiemycin is shown in FIG. 2. The three aromatic protons of $\epsilon$-rhodomycinone appear as doublets of doublet (dd) centered at 7.37 (J=8, 2 Hz), triplet centered at 7.76 (J=8 Hz) and another pair of doublets (dd) centered at 7.83 ppm (J=8, 2 Hz). The C-7 proton appears as a broad signal at 5.44 ppm (goes to a triplet (J=4 Hz) on D$_2$O shake), and the C-10 proton appears at 4.36 ppm. The two methylene groups C-13 and C-8 appear at 1.76 (m, J=7 Hz) and 2.36 ppm (d, J=4 Hz). The methyl groups appear at 1.23 (t, J=7 Hz) and 3.81 ppm. The phenolic hydroxyls appear at 12.14, 12.97 and 13.50 ppm.

A comparison of these data with maggiemycin $^1$H NMR (FIGS. 1 and 2) clearly reveals that there is no proton at C-7 in the maggiemycin structure. Because of this change, the C-8 methylene protons appear at 2.8 (1H, dd, J=17, 2 Hz) and 3.20 ppm (1H, d, J=17 Hz). The coupling between one of the C-8 protons and the C-10 proton was confirmed by spin decoupling studies. This suggests that $\epsilon$-rhodomycinone and maggiemycin are different only in the substitution pattern in ring A.

Figure 3:
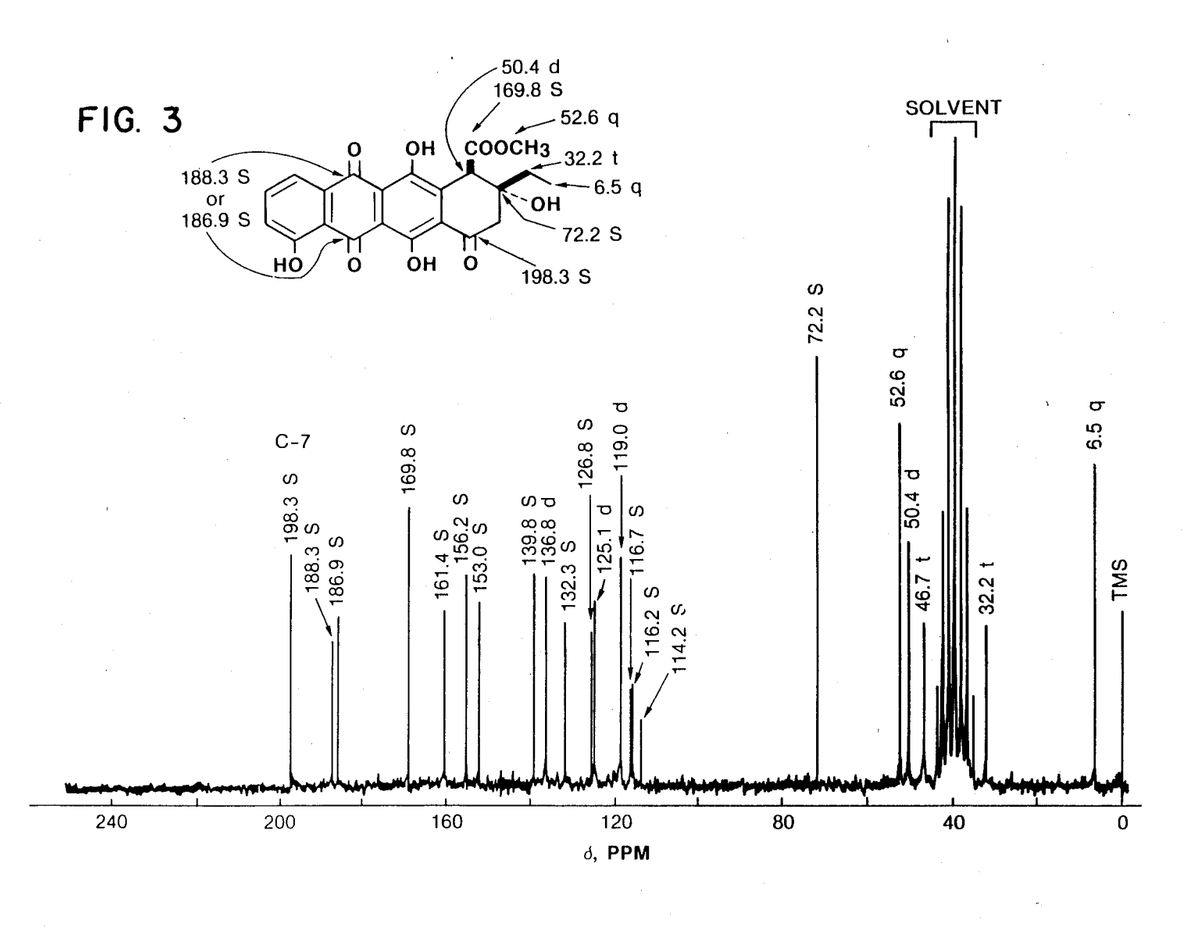
FIG. 3 is the $^1$H decoupled carbon-13 nuclear magnetic resonance spectrum ($^{13}$C NMR, FX-60, DMSO-d$_6$) of maggiemycin.

The $^{13}$C NMR spectrum of maggiemycin (FIG. 3) was instrumental in distinguishing between these two structures. A signal at 198.3 ppm clearly establishes the structure for maggiemycin (see FIG. 3). The assignment of other important signals is also indicated in FIG. 3.

Figure 4:
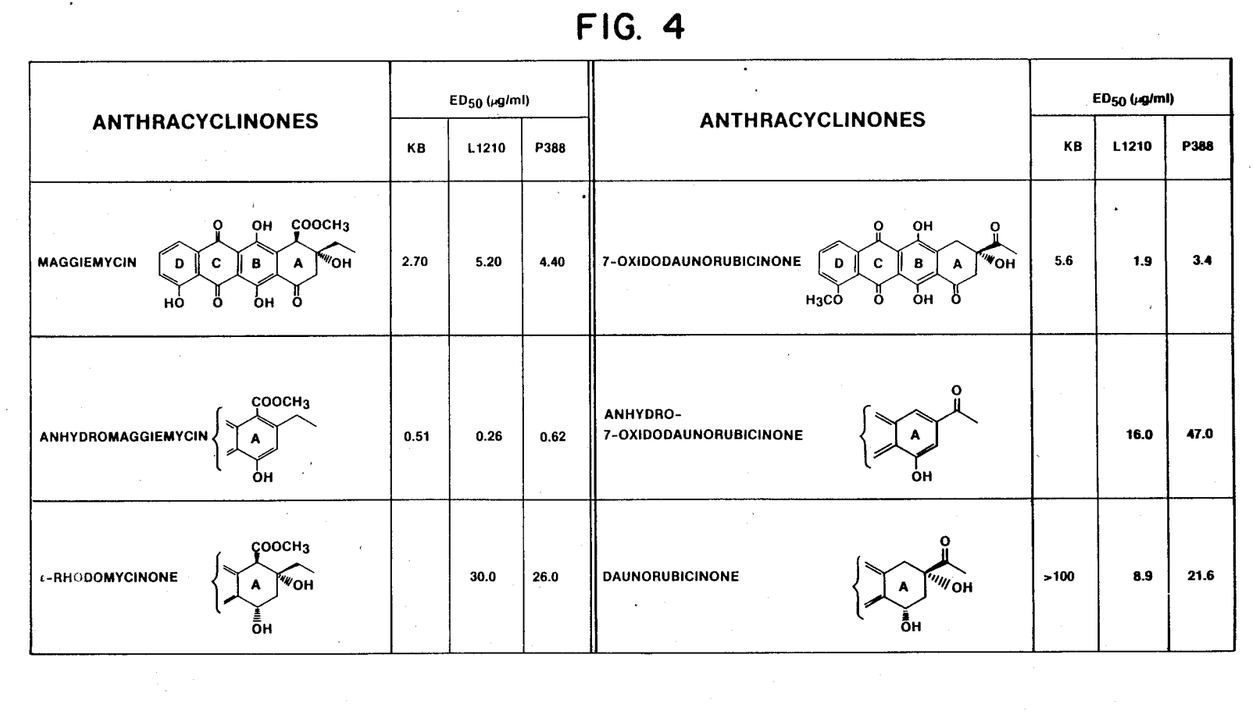
FIG. 4 is a structure-activity comparison of maggiemycin, and anhydromaggiemycin, $\epsilon$-rhodomycinone, 7-oxidodaunorubicinone, anhydro-7-oxidodaunorubicinone, and daunorubicinone.
Figure 5:
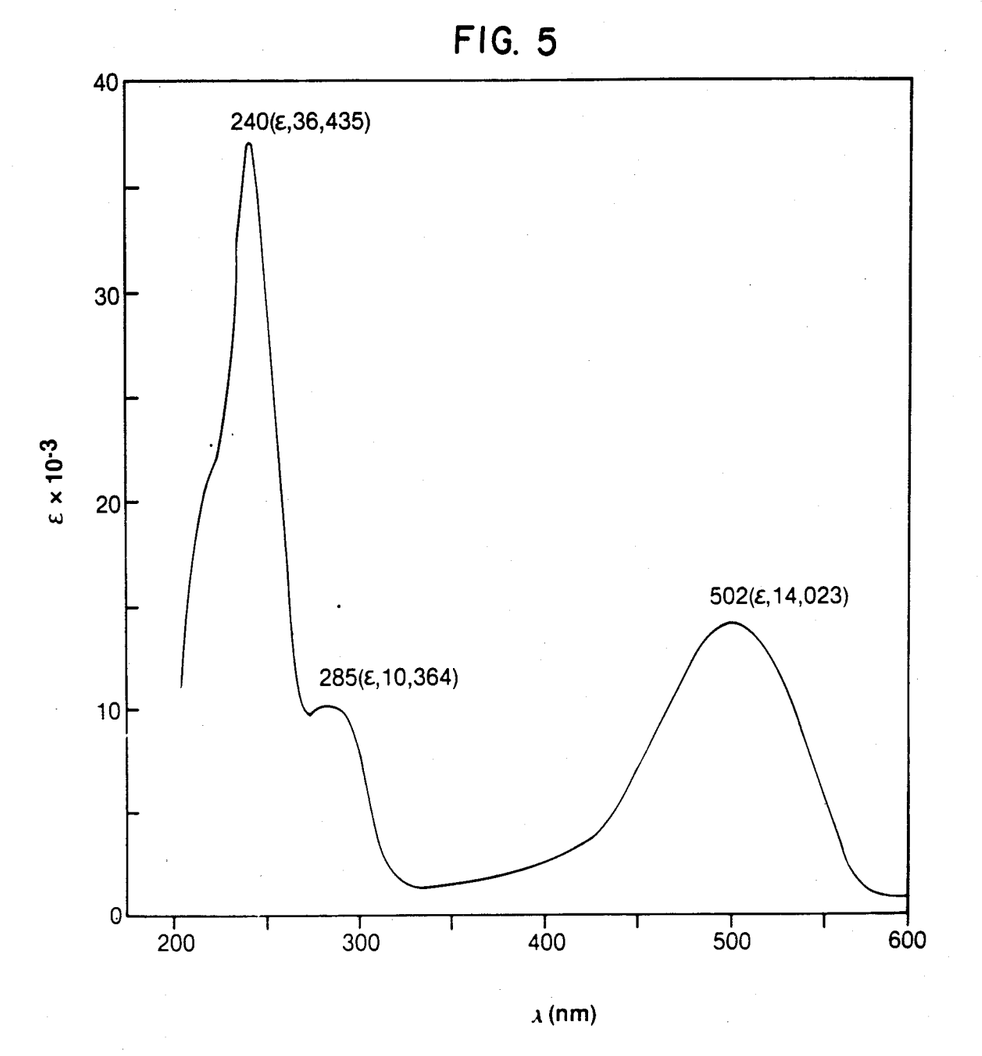
FIG. 5 is the ultraviolet-visible spectrum of maggiemycin.
Figure 6:
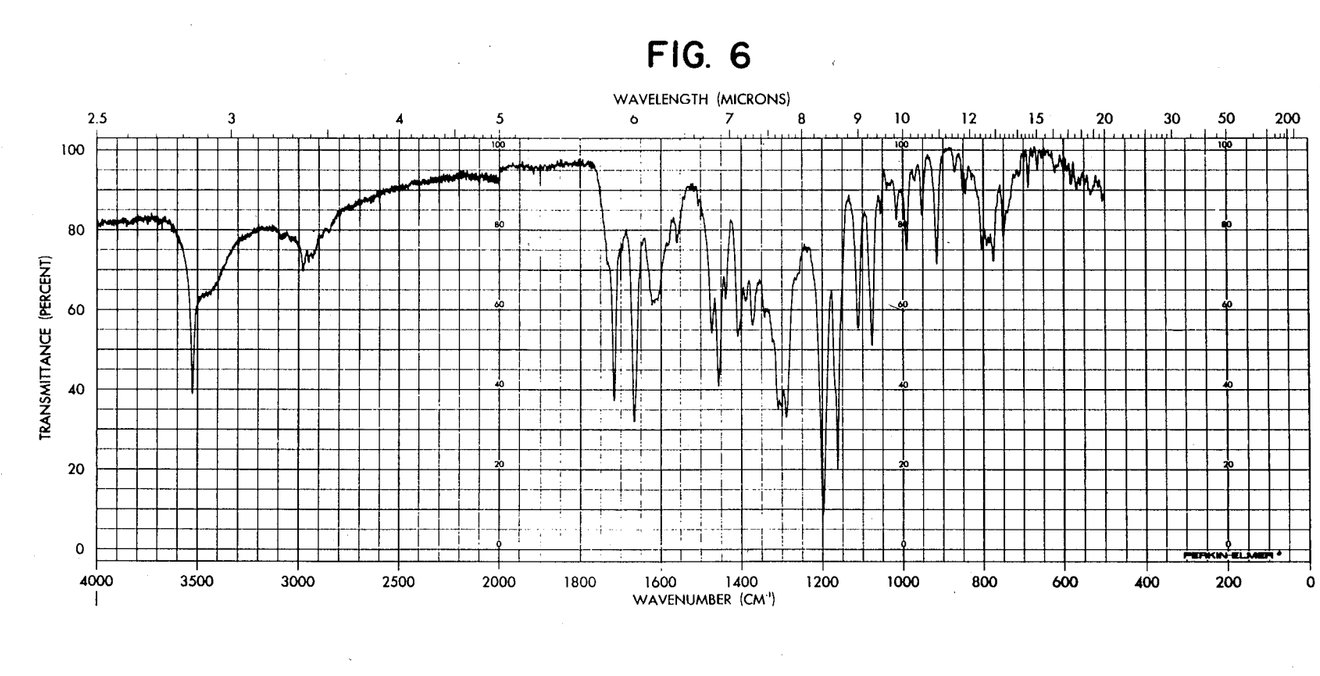
FIG. 6 is the infra-red spectrum of maggiemycin.
Figure 7:
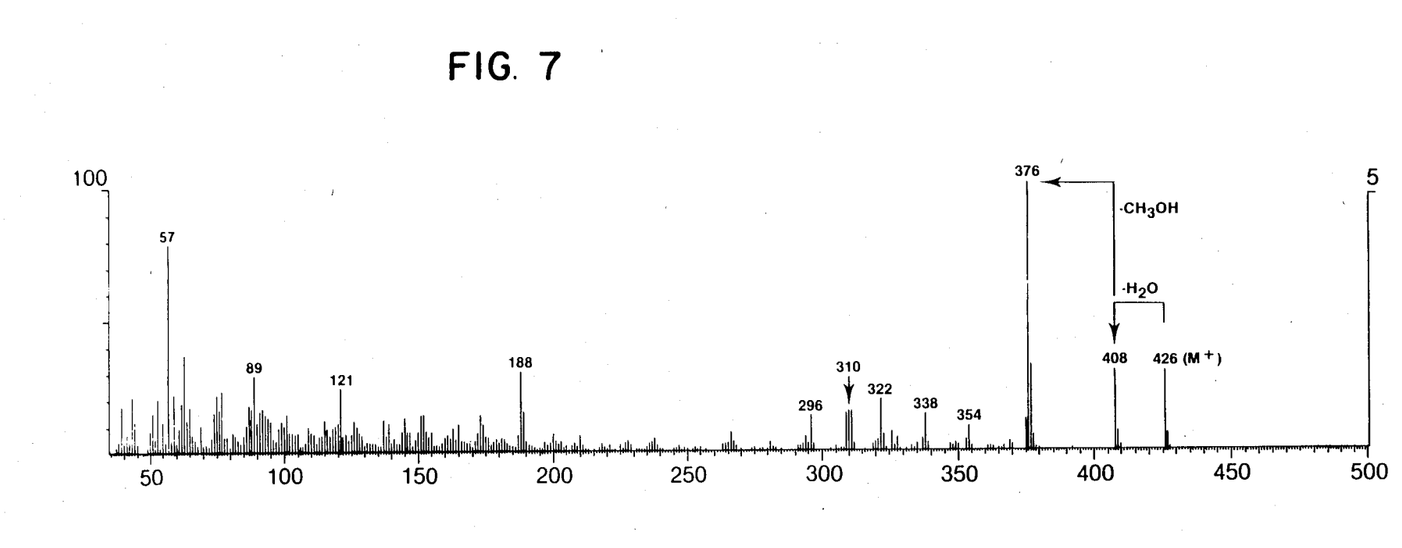
FIG. 7 is the electron impact mass spectrum of maggiemycin.

Further comparison of the $^1$H NMR spectra of $\epsilon$-rhodomycinone (see FIG. 2) and maggiemycin (FIG. 3) with the $^1$H NMR of anhydromaggiemycin (FIG. 2) clearly shows the absence of C-7 and C-10 protons and also the methylene grouping at C-8 in anhydromaggiemycin. The most characteristic peak in the spectrum was a new singlet in the aromatic region at 7.22 ppm, which was not present in the other two compounds. Based on the elemental composition (Table 2) and the above $^1$H NMR data the only possible structure for anhydromaggiemycin is shown in FIG. 4.

Partial synthesis of maggiemycin and anhydromaggiemycin

The structure of maggiemycin and anhydromaggiemycin were confirmed by their partial synthesis from, and thus correlation with $\epsilon$-rhodomycinone.

$\epsilon$-Rhodomycinone, a by-product of daunorubicin fermentations, was first isolated by extraction and column chromatography over silica gel and identified by comparison of infra-red (IR), proton nuclear magnetic resonance ($^1$H NMR), carbon-13 nuclear magnetic resonance ($^{13}$C NMR) spectra and electron impact mass spectrum (EIMS) with an authentic sample and was used for the synthesis.

Treatment of $\epsilon$-rhodomycinone with Jones reagent in acetone produced a yield of 68% maggiemycin. The product was isolated by extraction with chloroform followed by silica gel chromatography. The synthetic material had TLC, ultraviolet (UV), IR, $^1$H NMR and EIMS identical to that of natural maggiemycin.

Figure 10:
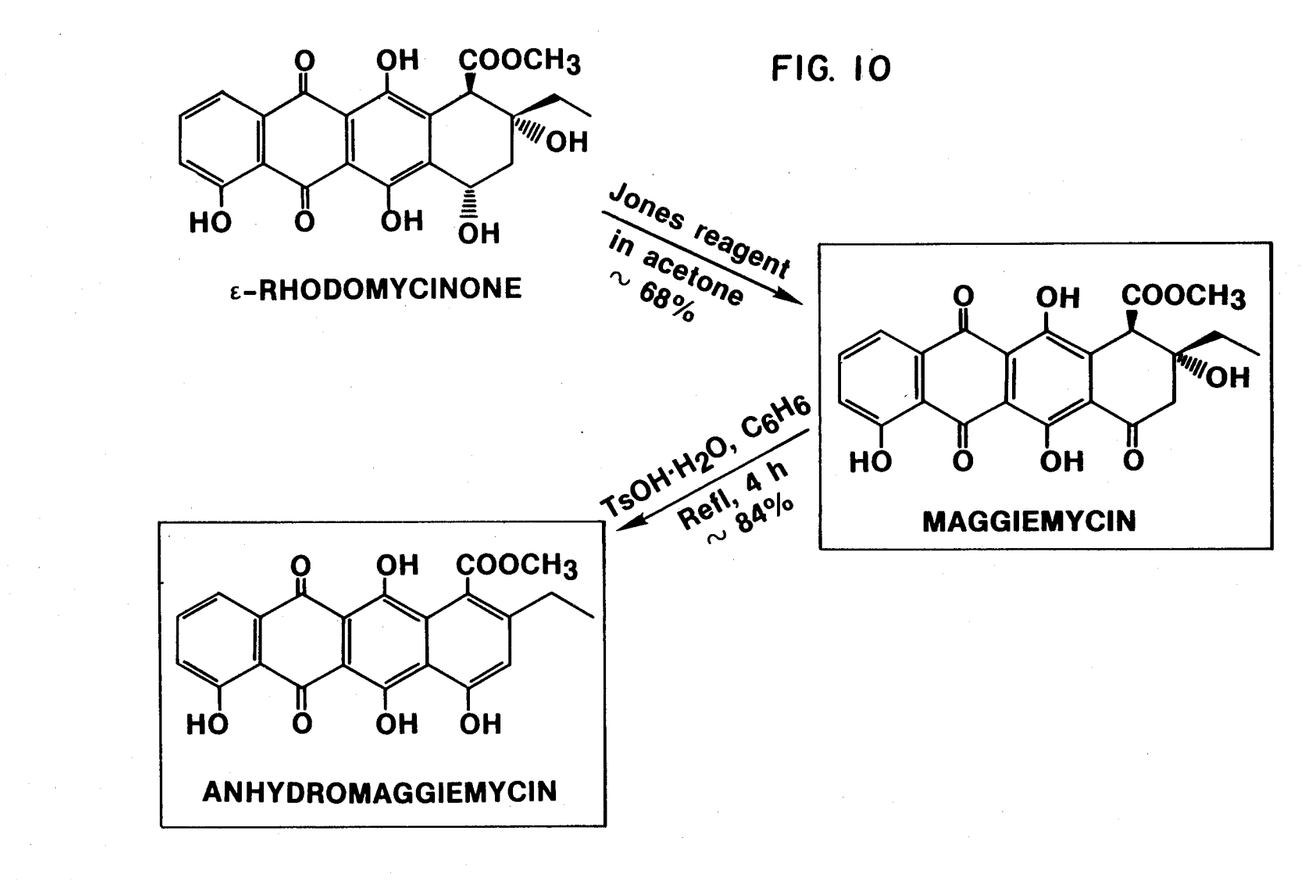
FIG. 10 is a flow scheme for the partial synthesis of maggiemycin and anhydromaggiemycin.

When maggiemycin was refluxed with p-toluene sulfonic acid in benzene for 4 hours, anhydromaggiemycin, at a yield of 84%, was obtained that was identical to the natural product in all physicochemical properties. The preparation of these compounds is summarized in FIG. 10.

Preparation of 7-oxidodaunorubicinone

Daunorubicinone was prepared from daunorubicin by mild acid hydrolysis. 7-oxidodaunorubicinone was prepared from daunorubicinone and Jones reagent ($Cr_2O_3$ and $H_2SO_4$) by stirring at 0° C. for 24 hours. The reaction product was extracted with chloroform, and the chloroform extract was washed with water and brine and dried over sodium sulfate. Sodium sulfate was removed by filtration, and the filtrate was concentrated under vacuum. The residue was purified over a silica gel column using chloroform-hexane-methanol as the eluent. The purified product was a red powder which had a melting point of 125°–127° C. Anal. calcd for $C_{21}H_{16}O_8$:mol. wt. 396. Found mol. wt. 396.

Preparation of Anhydro-7-Oxidodaunorubicinone

Anhydro-7-oxidodaunorubicinone was prepared from 7-oxidodaunorubicinone by mixing with p-toluene sulfonic acid and benzene and refluxing using a Dean stark trap to remove water formed in the reaction mixture. After the reaction was completed, the reaction mixture was cooled, diluted with water, and benzene and aqueous layers were separated. The benzene layer was washed with water and dried over sodium sulfate. Sodium sulfate was removed by filtration, and the filtrate was concentrated under vacuum. Removal of solvent and precipitation of the residue from chloroform-petroleum ether produced a pure product, having a melting point 275°–279° C.

Structure-activity relationship

The biological activity of these newly isolated anthracyclinones was compared with some of the known anthracyclinones. Each compounds was tested for in vitro activity against one or all of the murine tumor cell lines KB, L1210 and P388. The results are summarized in FIG. 4. In the ε-rhodomycinone series, ε-rhodomycinone was inactive, whereas maggiemycin and anhydromaggiemycin were active, the latter being more active. In the daunorubicinone series daunorubicinone and anhydro-7-oxidodaunorubicinone were inactive, whereas 7-oxidodaunorubicinone was active.

Additional details of our invention were set forth in our presentation at the 21st Interscience Conference on Antimicrobial Agents and Chemotherapy, Chicago, Ill. (November 1981), and in our paper entitled "Maggiemycin and Anhydromaggiemycin: Two Novel Anthracyclinone Antitumor Antibiotics. Isolation, Structures, Partial Synthesis and Biological Properties" to be submitted for publication to *J. Antibiotics,* both of which are incorporated herein by reference.

EXAMPLE 1

Derivation and Fermentation of Variant Strain PDJ566-A21

All strains were derived from a culture of an unspeciated Streptomyces designated PD J566 according to KERN, D. L.; R. H. BUNGE, J. C. FRENCH & H. W. DION: The identification of ε-rhodomycinone and 7-deoxy-daunorubicinol aglycone in daunorubicin beers. *J. Antibiotics* 30; 432–434 (1977), herein incorporated by reference. Strain V1 was isolated as the predominant colony with morphological type of PD J566. Strain A21 was isolated as a natural variant of Strain V1, recognizable as a blue colony among the normal red colonies of strain V1. Strains were maintained as spore suspensions in 10% glycerol, 0.5% Tween 80 at a temperature of −196° C.

Fermentations were initiated by transferring 0.05 to 0.5 ml of a spore suspension to a baffled shake flask containing 1/5 of the nominal flask volume of seed medium (Medium S). Medium S. contained (w/v): 1.5% corn starch, 0.5% Pharmamedia (Traders Protein, Fort Worth, Tex.), 0.5% Nutrisoy defatted soy flour (Archer-Daniels Midland Co., Decatur, Ill.), 0.1% Red Star autolyzed yeast (Universal Foods Corp., Milwaukee, Wis.), 0.25% sodium chloride, and 0.5% calcium.

Seed cultures were incubated for 3 days at 28° to 30° C. on a 1″ stroke rotary shaker at 250 rpm. Seed cultures were then used to inoculate (at a ratio of 10% v/v) baffled shake flasks containing 1/5 of the nominal flask volume of production medium (Medium P). Medium P contained (w/v): 5% glucose monohydrate, 1.2% herring meal (The Mearl Corp., Eastport, Maine, 0.5% Red Star autolyzed yeast, 1.25% Nutrisoy, 0.33% sodium chloride, 1.0% calcium carbonate and 0.2% (v/v) Prochem 51 (Prochem Co., Guonee, Ill.). Production cultures are incubated for 7 days at 28° to 30° C. with rotary shaking at 250 rpm (1″ stroke).

Large-scale production runs were done in 14-liter microferms (New Brunswick Scientific Co.) containing 10 liters of medium P, but with 2% (v/v) Prochem 51. Fermentations were run for seven days at 30° C. with an aeration rate of 5 liters/min. and an agitation rate of 500 rpm.

EXAMPLE 2

Isolation of maggiemycin and anhydromaggiemycin

At the end of the fermentation of Example 1, cultures were supplemented 8 g/l of Celite (an inert filter aid; Johns-Manville Co.) and the aqueous phase was removed by filtration through Whatman #1 filter paper and discarded. The mycelial filter cake was extracted with ⅓ of the original culture volume of a mixture of ethanol-water-concentrated hydrochloric acid (12:6:1). The extract was recovered by filtration through Whatman #1 filter paper and the filter cake was re-extracted twice as above. The three extract filtrates were pooled and 2 liters aliquots were supplemented with 2 liters of tap water, then extracted three times with chloroform volumes of 200 ml, 100 ml and a final 100 ml. The chloroform phases were recovered, pooled, and concentrated by evaporation in vacuo at 40° C. to produce the crude compound.

The crude compound (about 600 mg) was dissolved in chloroform and loaded onto a TLC grade silica gel column (6.5 cm×29 cm). The column was eluted with chloroform (100%, 100×10 ml, discarded); chloroform-acetic acid (99:1, 146×10 ml., discarded), 21×10 ml, pure red compound), (14×10 ml, mixture); chloroform-acetic acid (98:2, 13×10 ml, pure purple compound) and chloroform-acetic acid (95:5, 90×10 ml, mixture).

In TLC, using chloroform or chloroform-acetic acid as the solvents, the purple compound moved faster, but on column the red compound eluted first. Every third fraction was checked by TLC and the pure red and purple fractions were mixed separately, concentrated and precipitated from chloroform-petroleum ether. The precipitates were washed with petroleum ether (3×10 ml) and dried under high vacuum to produce a red and purple powder. See FIG. 9. The red powder (198.8 mg) was designated as maggiemycin (NSC-D344012) and had the first mp 190°–195° C. at which time needles begin to form which melt at 250° C.; $[\alpha]_D^{21} +4.6°$ (≦0.1, Dioxane).

The purple powder (128 mg) was designated as anhydromaggiemycin and had mp 252°–256° C.

The A21 variant strain of streptomyces PD J566 has been deposited at the American Type Culture Collection, situated at 12301 Parklawn Drive, Rockville, Md., on or before the filing date of this application, and has received the ATCC designation number of 39235.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. Maggiemycin, and physiologically acceptable salts thereof.

2. Anhydromaggiemycin, and physiologically acceptable salts thereof.

3. A process for the preparation of maggiemycin as claimed in claim 1, comprising:
   (a) fermenting streptomyces variant strain PD J566-A21;
   (b) extracting cellular material with an acidic polar solvent, and filtering;
   (c) subjecting the filtrate to extraction with a polar solvent to yield an extract;
   (d) washing the extract with water;
   (e) concentrating; and
   (f) purifying by chromatography to yield a red powder maggiemycin.

4. A process for the preparation of anhydromaggiemycin as claimed in claim 2, comprising:
   (a) fermenting streptomyces variant strain PD J566-A21;
   (b) extracting cellular material with an acidic polar solvent, and filtering;
   (c) subjecting the filtrate to extraction with a polar solvent to yield an extract;
   (d) washing the extract with water;
   (e) concentrating; and
   (f) purifying by chromatography to yield a purple powder anhydromaggiemycin.

* * * * *